(12) United States Patent
Tsaur

(10) Patent No.: US 7,416,355 B2
(45) Date of Patent: Aug. 26, 2008

(54) CONTAINER AND APPLICATOR

(76) Inventor: Garry Tsaur, 19222 Tranbarger St., Rowland Heights, CA (US) 91748

( * ) Notice: Subject to any disclaimer, the term of this patent is extended or adjusted under 35 U.S.C. 154(b) by 120 days.

(21) Appl. No.: 10/425,791

(22) Filed: Apr. 29, 2003

(65) Prior Publication Data

US 2004/0218965 A1    Nov. 4, 2004

(51) Int. Cl.
*A46B 11/00*    (2006.01)

(52) U.S. Cl. ........................ 401/119; 401/132

(58) Field of Classification Search ......... 401/132–135, 401/119, 118, 178, 170; 604/1–3; 222/187
See application file for complete search history.

(56) References Cited

U.S. PATENT DOCUMENTS

| | | | |
|---|---|---|---|
| 876,090 A * | 1/1908 | Prescott | 401/170 |
| 2,809,386 A * | 10/1957 | Asturias, Jr. | 401/170 |
| 3,227,165 A * | 1/1966 | Costanza | 401/178 |
| 3,703,765 A * | 11/1972 | Perez | 30/41 |
| 4,875,602 A * | 10/1989 | Chickering et al. | 222/187 |
| 5,120,301 A * | 6/1992 | Wu | 604/3 |
| 5,152,742 A * | 10/1992 | Simpson | 604/3 |
| 5,266,266 A * | 11/1993 | Nason | 422/58 |
| 5,702,035 A * | 12/1997 | Tsao | 222/187 |
| 5,927,884 A * | 7/1999 | Kao | 401/132 |
| 6,467,982 B1 * | 10/2002 | Tsao | 401/263 |

* cited by examiner

*Primary Examiner*—Huyen Le
(74) *Attorney, Agent, or Firm*—Joe Nieh

(57) ABSTRACT

A small slender container and an applicator that may be used to store small quantity of substance, such as creams, lotions, and make-ups in a sealed environment and easily and sanitarily dispenses its content for application as desired is disclosed. The content of the slender container may be permanently sealed with an opening means or may be sealed with a high viscosity substance such as silicone. The container and applicator comprises of a small slender container with a sealed first end and a second end with a high viscosity substance sealed within the container and an applicator that is inserted into the container to simultaneously extract and inject the content into the applicator. The applicator may then be used to apply the contents to the desired location. After application, the sealed compartment and the applicator are disposed of.

6 Claims, 2 Drawing Sheets

US 7,416,355 B2

CONTAINER AND APPLICATOR

BACKGROUND

1. Field of Invention

The present invention relates to a small sealed container and an applicator. More specifically, the present invention relates to a small slender container designed to be used with an applicator such as a cotton swab.

2. Description of Related Art

Small containers in the general form of an elongated tube may be used to distribute and/or apply small quantities of products such as creams, lotions, and make-ups. The small container's contents are generally difficult to extract, particularly if the viscosity of the content is high. Therefore, either the remaining contents are disposed of or some form of applicator or extractor must be used to extract the contents.

Often, an applicator is required to retrieve and accurately apply the content of the container to the desired location. The applicator is generally a separate component that is inserted into the container to retrieve the content and then applied to the desired location. Some applicators are incorporated into the cap of the container such that when the cap is removed, the applicator is exposed and can be used to retrieve and apply the content of the container. Other applicators are completely separate from the container such that it is not a part of the container.

U.S. Pat. No. 5,702,035, Slender Tubular Container with Opening and Closing Means, is one of applicant's patented containers and is one example of a container with applicator for liquids. A more effective design is required for high viscosity contents.

SUMMARY OF THE INVENTION

The present invention is a small slender container and an applicator that may be used to store small quantity of substance, such as creams, lotions, and make-ups in a sealed environment and easily and sanitarily dispenses its content for application as desired. The content of the slender container may be permanently sealed with an opening means or may be sealed with a high viscosity substance such as silicone. The container and applicator comprises of a small slender container with a sealed first end and a second end with a high viscosity substance sealed within the container and an applicator that is inserted into the container to simultaneously extract and inject the content into the applicator. The applicator may then be used to apply the contents to the desired location. After application, the sealed compartment and the applicator are disposed of.

DETAILED DESCRIPTION OF THE PREFERRED EMBODIMENT

Figure 1:
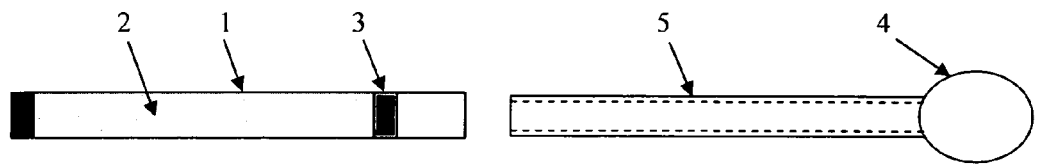
FIG. 1 shows the preferred embodiment of the container and applicator.

FIG. 1 shows the preferred embodiment of the container and applicator. The preferred embodiment of the container and applicator comprises an essentially constant inside diameter elongated housing elongated housing 1 with a first sealed end and a second open end. A substance 2 such as cream, lotion, make-up, or other liquid is contained within the elongated housing 1 near the first sealed end. If the substance 2 is evaporative, a high viscosity sealer 3 such as silicone may be used to separate the substance 2 from the second open end to prevent evaporation. An applicator 4 is affixed to the first end of a hollow tube 5. When the second end of the hollow tube 5 with the applicator 4 is inserted into the elongated housing 1, the contents of the elongated housing 1 will be forced into the applicator 4 through the hollow tube 5 with the applicator 4 due to the displacement of the content in the elongated housing 1 by the inserted hollow tube 5.

Figure 2:
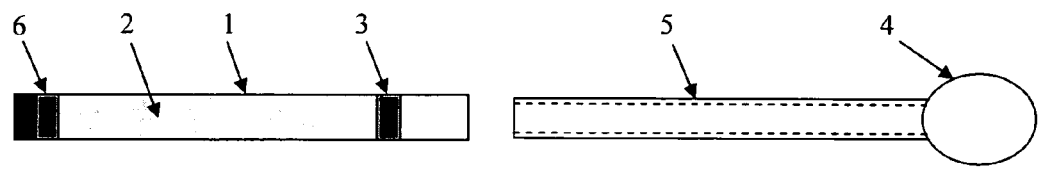
FIG. 2 shows another embodiment of the container and applicator.

FIG. 2 shows another embodiment of the container and applicator. In this embodiment, the container and applicator comprises an elongated housing 1 with a first sealed end and a second open end. A substance 2 such as cream, lotion, make-up, or other liquid is contained within the elongated housing 1 near the first sealed end separated from the first sealed end with a high viscosity substance 6 such as silicone. If the substance 2 is evaporative, another high viscosity sealer 3 such as silicone may be used to separate the substance 2 from the second open end to prevent evaporation. An applicator 4 is affixed to the first end of a hollow tube 5. When the second end of the hollow tube 5 with the applicator 4 is inserted into the elongated housing 1, the contents of the elongated housing 1 will be forced into the applicator 4 through the hollow tube 5 with the applicator 4 due to the displacement of the content in the elongated housing 1 by the inserted hollow tube 5. The high viscosity substance 6 near the first sealed end is the last to enter the hollow tube 5 and is designed to force the remaining content of the elongated housing 1 out of the inserted hollow tube 5 and into the applicator 4.

Figure 3:
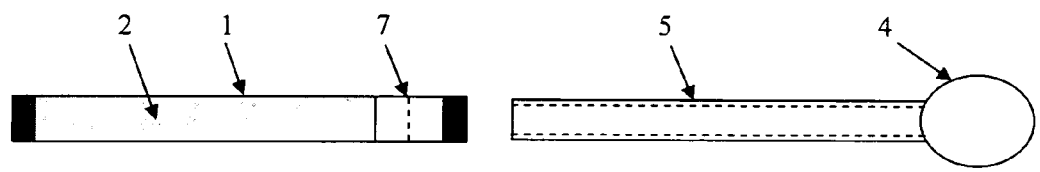
FIG. 3 shows another embodiment of the container and applicator.

FIG. 3 shows another embodiment of the container and applicator. In this embodiment, the container and applicator comprises an elongated housing 1 with a first sealed end and a second sealed end with an opening means 7 near the second sealed end. A substance 2 such as cream, lotion, make-up, or other liquid is contained within the elongated housing 1 near the first sealed end. An applicator 4 is affixed to the first end of a hollow tube 5. When the second end of the hollow tube 5 with the applicator 4 is inserted into the elongated housing 1 after the elongated housing 1 is opened through the opening means 7 near the second sealed end of the elongated housing 1, the contents of the elongated housing 1 will be forced into the applicator 4 through the hollow tube 5 with the applicator 4 due to the displacement of the content in the elongated housing 1 by the inserted hollow tube 5.

Figure 4:
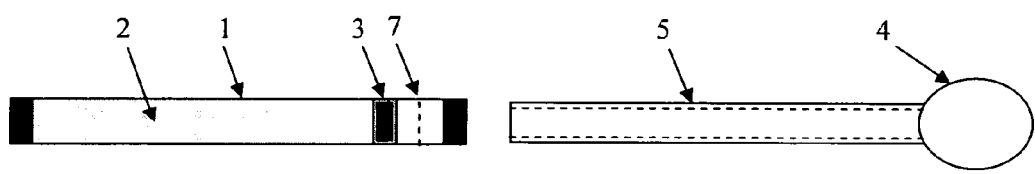
FIG. 4 shows another embodiment of the container and applicator.

FIG. 4 shows another embodiment of the container and applicator. In this embodiment, the container and applicator comprises an elongated housing 1 with a first sealed end and a second sealed end with an opening means 7 near the second sealed end. A substance 2 such as cream, lotion, make-up, or other liquid is contained within the elongated housing 1 near the first sealed end. If the substance 2 has low viscosity, a high viscosity sealer 3 such as silicone may be used to separate the substance 2 from the second sealed end to retain the substance 2 near the first sealed end. An applicator 4 is affixed to the first end of a hollow tube 5. When the second end of the hollow tube 5 with the applicator 4 is inserted into the elongated housing 1 after the elongated housing 1 is opened through the opening means 7 near the second sealed end of the elongated housing 1, the contents of the elongated housing 1 will be forced into the applicator 4 through the hollow tube 5 with the applicator 4 due to the displacement of the content in the elongated housing 1 by the inserted hollow tube 5.

Figure 5:
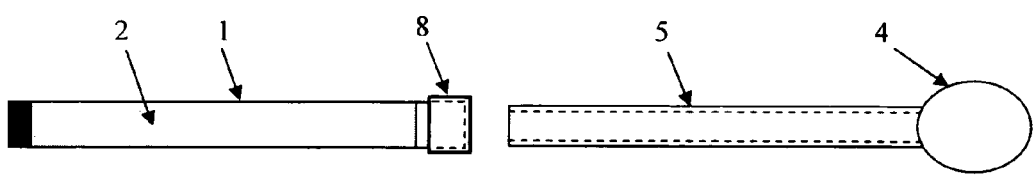
FIG. 5 shows another embodiment of the container and applicator.

FIG. 5 shows another embodiment of the container and applicator. In this embodiment, the container and applicator comprises an elongated housing 1 with a first sealed end and a second end with an opening means 8 such as a screw-on cap. A substance 2 such as cream, lotion, make-up, or other liquid is contained within the elongated housing 1 near the first sealed end. An applicator 4 is affixed to the first end of a hollow tube 5. When the second end of the hollow tube 5 with the applicator 4 is inserted into the elongated housing 1 after the elongated housing 1 is opened through the opening means 8 at the second end of the elongated housing 1, the contents of the elongated housing 1 will be forced into the applicator 4 through the hollow tube 5 with the applicator 4 due to the displacement of the content in the elongated housing 1 by the inserted hollow tube 5.

Figure 6:
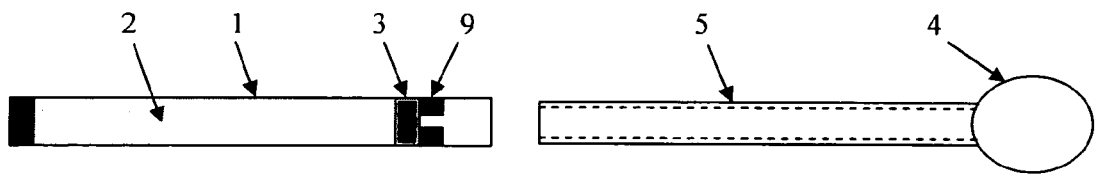
FIG. 6 shows another embodiment of the container and applicator.

FIG. 6 shows another embodiment of the container and applicator. In this embodiment, the container and applicator comprises an elongated housing 1 with a first sealed end and a second open end. A substance 2 such as cream, lotion, make-up, or other liquid is contained within the elongated housing 1 near the first sealed end. If the substance 2 is evaporative, a high viscosity sealer 3 such as silicone may be used to separate the substance 2 from the second open end to prevent evaporation. A plug 9 with a hole through its center is placed immediately next to the substance 2 or the high viscosity sealer 3, if one is utilized. An applicator 4 is affixed to the first end of a hollow tube 5. When the second end of the hollow tube 5 with the applicator 4 is inserted into the elongated housing 1, the hollow tube 5 will force the plug 9 to apply pressure and scrub the contents of the elongated housing 1 from the inside walls of the elongated housing 1 to fully force all the contents into the applicator 4 through the hollow tube 5 with the applicator 4 due to the displacement of the content by the inserted hollow tube 5.

Figure 7A:
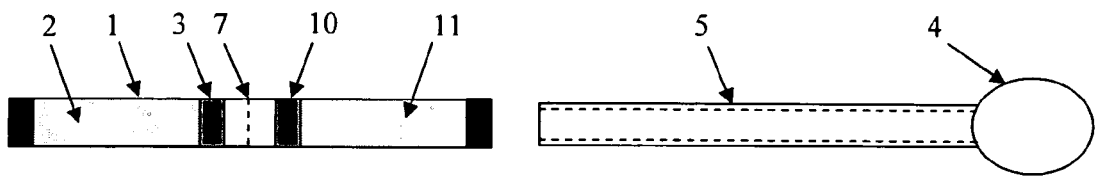
FIG. 7a shows another embodiment of the container and applicator.

FIG. 7a shows another embodiment of the container and applicator. In this embodiment, the container and applicator comprises an elongated housing 1 with a first sealed end and a second sealed end with an opening means 7 between the first sealed end and the second sealed end. A substance 2 such as cream, lotion, make-up, or other liquid is contained within the elongated housing 1 near the first sealed end separated from the opening means 7 with a high viscosity substance 3 such as silicone. A substance 11 such as cream, lotion, make-up, or other liquid is contained within the elongated housing 1 near the second sealed end separated from the opening means 7 with a high viscosity substance 10 such as silicone. An applicator 4 is affixed to the first end of a hollow tube 5. When the second end of the hollow tube 5 with the applicator 4 is inserted into either end of the elongated housing 1 after the elongated housing 1 is opened through the opening means 7, the contents of the elongated housing 1 will be forced into the applicator 4 through the hollow tube 5 with the applicator 4 due to the displacement of the content in the elongated housing 1 by the inserted hollow tube 5. The substance 2 in elongated housing 1 near the first sealed end may be the same as or a different substance than the substance 11 near the second sealed end.

Figure 7B:
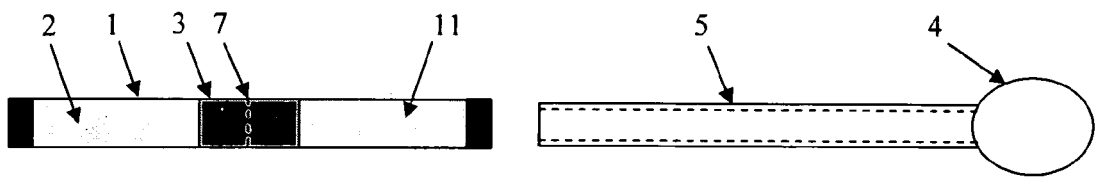
FIG. 7b shows another embodiment of the container and applicator.

FIG. 7b shows another embodiment of the container and applicator. In this embodiment, the container and applicator comprises an elongated housing 1 with a first sealed end and a second sealed end with an opening means 7 between the first sealed end and the second sealed end. A substance 2 such as cream, lotion, make-up, or other liquid is contained within the elongated housing 1 near the first sealed end separated from substance 11 near the second sealed end with a high viscosity substance 3 such as silicone with an opening means 7 at the location of the high viscosity substance 3. An applicator 4 is affixed to the first end of a hollow tube 5. When the second end of the hollow tube 5 with the applicator 4 is inserted into either end of the elongated housing 1 after the elongated housing 1 is opened through the opening means 7, the contents of the elongated housing 1 will be forced into the applicator 4 through the hollow tube 5 with the applicator 4 due to the displacement of the content in the elongated housing 1 by the inserted hollow tube 5. The substance 2 in elongated housing 1 near the first sealed end may be the same as or a different substance than the substance 11 near the second sealed end.

Figure 8:
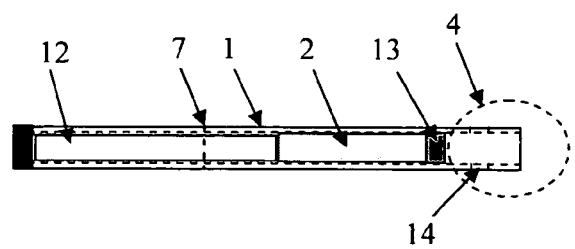
FIG. 8 shows another embodiment of the container and applicator.

FIG. 8 shows another embodiment of the container and applicator. In this embodiment, the container and applicator comprises an elongated housing 1 with a first sealed end and a second open end. One or more small holes 14 are located on the elongated housing 1 near the second open end. An elongated member 12 with at least one sealed end is inserted into the elongated housing 1 and rests on the first sealed end. An opening means 7 on the elongated housing 1 is located at a predetermined location along the position of the elongated member 12. A substance 2 such as cream, lotion, make-up, or other liquid is contained within the elongated housing 1 near the sealed end of the elongated member 12. If the substance 2 is evaporative, a high viscosity sealer 13 such as silicone may be used to separate the substance 2 from the second open end to prevent evaporation. An applicator 4 may be affixed to the second open end of the elongated housing 1. When the elongated housing 1 is opened through the opening means 7, the elongated member 12 is exposed and can be depressed to extract the content of the elongated housing 1 into the applicator 4.

Figure 9:
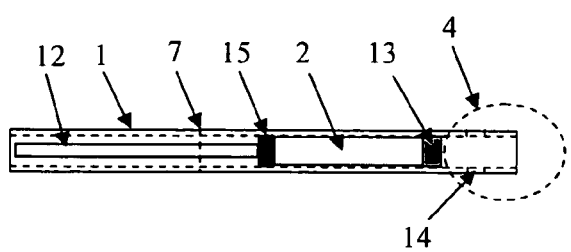
FIG. 9 shows another embodiment of the container and applicator.

FIG. 9 shows another embodiment of the container and applicator. In this embodiment, the container and applicator comprises an elongated housing 1 with a first open end and a second open end. One or more small holes 14 are located on the elongated housing 1 near the second open end. An elongated member 12 is inserted into the elongated housing 1 and positioned near the first open end. An opening means 7 on the elongated housing 1 is located at a predetermined location along the position of the elongated member 12. A stopper 15 is attached to the end of the elongated member 12 near the second open end. A substance 2 such as cream, lotion, make-up, or other liquid is contained within the elongated housing 1 near the stopped 15 at the end of the elongated member 12. If the substance 2 is evaporative, a high viscosity sealer 13 such as silicone or a rubber stopper may be used to separate the substance 2 from the second open end to prevent evaporation. An applicator 4 may be affixed to the second open end of the elongated housing 1. When the elongated housing 1 is opened through the opening means 7, the elongated member 12 is exposed and can be depressed to extract the content of the elongated housing 1 into the applicator 4 through the one or more holes 14 near the end of the second open end.

Although the description above contains many specificities, these should not be construed as limiting the scope of the invention but as merely providing illustrations of some of the presently preferred embodiments of this invention. Thus the scope of the invention should be determined by the appended claims and their legal equivalents, rather than by the examples given.

What is claimed is:

1. A container and applicator comprising an elongated housing with a first sealed end and a second open end containing a substance near the first sealed end and a high viscosity substance placed between the substance in the elongated housing and the second open end to prevent evaporation of the substance and a hollow tube with a first end and a second end wherein when said second end of the hollow tube is inserted into the elongated housing the contents of the elongated housing will be forced through the hollow tube due to the displacement of the content by the inserted hollow tube.

2. A container and applicator as in claim 1, wherein a plug defining a hole through its center is placed between the high viscosity substance in the elongated housing and the second open end.

3. A container and applicator as in claim 1, wherein a high viscosity substance is placed at the sealed first end separating the substance from the sealed first end.

4. A container and applicator as in claim 1, wherein said second open end is sealed and an opening means is provided near said sealed second open end.

5. A container and applicator as in claim 1, wherein a removable cap is affixed to said second open end.

6. A container and applicator comprising an elongated housing with a first sealed end and a second open end containing a substance near the first sealed end and a high viscosity substance placed at the sealed first end separating the substance from the sealed first end and a hollow tube with a first end and a second end wherein when said second end of the hollow tube is inserted into the elongated housing the contents of the elongated housing will be forced through the hollow tube due to the displacement of the content by the inserted hollow tube.

* * * * *